(12) United States Patent
Fieselmann et al.

(10) Patent No.: US 10,383,591 B2
(45) Date of Patent: Aug. 20, 2019

(54) AUTOMATIC DETERMINATION OF JOINT LOAD INFORMATION

(71) Applicants: Andreas Fieselmann, Erlangen (DE); Anna Jerebko, Hausen (DE)

(72) Inventors: Andreas Fieselmann, Erlangen (DE); Anna Jerebko, Hausen (DE)

(73) Assignee: Siemens Healthcare GmbH, Erlangen (DE)

( * ) Notice: Subject to any disclaimer, the term of this patent is extended or adjusted under 35 U.S.C. 154(b) by 85 days.

(21) Appl. No.: 15/401,524

(22) Filed: Jan. 9, 2017

(65) Prior Publication Data
US 2017/0196526 A1    Jul. 13, 2017

(30) Foreign Application Priority Data
Jan. 11, 2016 (DE) .......................... 10 2016 200 202

(51) Int. Cl.
| | | |
|---|---|---|
| *A61B 5/05* | (2006.01) | |
| *H04N 9/47* | (2006.01) | |
| *H04N 7/18* | (2006.01) | |
| *A61B 6/00* | (2006.01) | |
| *A61B 5/11* | (2006.01) | |
| *A61B 5/00* | (2006.01) | |
| *A61B 6/04* | (2006.01) | |
| *G06K 9/00* | (2006.01) | |

(Continued)

(52) U.S. Cl.
CPC ............ *A61B 6/505* (2013.01); *A61B 5/1121* (2013.01); *A61B 5/4528* (2013.01); *A61B 6/0407* (2013.01); *A61B 6/5217* (2013.01); *G06K 9/00362* (2013.01); *G06T 7/0012* (2013.01); *G01G 19/44* (2013.01); *G06T 2207/10012* (2013.01); *G06T 2207/10116* (2013.01)

(58) Field of Classification Search
CPC .................................................... A61B 5/4528
See application file for complete search history.

(56) References Cited

U.S. PATENT DOCUMENTS

| | | | |
|---|---|---|---|
| 6,560,477 B1 * | 5/2003 | Filler | A61B 5/055 |
| | | | 324/309 |
| 7,239,908 B1 * | 7/2007 | Alexander | A61B 5/055 |
| | | | 378/21 |

(Continued)

FOREIGN PATENT DOCUMENTS

| | | |
|---|---|---|
| DE | 102013109057 A1 | 2/2015 |
| WO | WO2014145267 A1 | 9/2014 |

OTHER PUBLICATIONS

German office Action for related German Application No. 10 2016 200 202.3 dated Aug. 29, 2016, with English Translation.

(Continued)

*Primary Examiner* — Rebecca A Volentine
(74) *Attorney, Agent, or Firm* — Lempia Summerfield Katz LLC

(57) ABSTRACT

A method is provided for the automatic determination of at least one joint load information item concerning a joint of a patient, wherein at least one image data set of the loaded joint is recorded by an imaging apparatus. Several image data sets of the joint, of which at least one is three-dimensional, are recorded in each case for different loading states by the imaging apparatus. By combined evaluation of the image data sets, the at least one joint load information item is determined.

23 Claims, 6 Drawing Sheets

(51) Int. Cl.
*G06T 7/00* (2017.01)
*G01G 19/44* (2006.01)

(56) References Cited

U.S. PATENT DOCUMENTS

| | | | |
|---|---|---|---|
| 9,865,095 B2* | 1/2018 | Gotte | G16H 50/50 |
| 2005/0113663 A1* | 5/2005 | Tamez-Pena | A61B 5/055 600/407 |
| 2007/0015995 A1* | 1/2007 | Lang | A61B 5/055 600/407 |
| 2007/0287900 A1* | 12/2007 | Breen | A61B 5/1116 600/407 |
| 2008/0139922 A1* | 6/2008 | Pelletier | A61B 5/055 600/410 |
| 2008/0285805 A1* | 11/2008 | Luinge | A61B 5/1114 382/107 |
| 2010/0067771 A1 | 3/2010 | Dahnke et al. | |
| 2014/0208578 A1 | 7/2014 | Linderman et al. | |
| 2015/0320341 A1 | 11/2015 | Breen et al. | |
| 2015/0327795 A1 | 11/2015 | Alexander et al. | |
| 2016/0140758 A1* | 5/2016 | Ooga | G06T 7/11 382/128 |

OTHER PUBLICATIONS

Hirschmann et al. "Upright CT of the knee: the effect of weight-bearing on joint alignment," Eur. Radiol., pp. 1-7, 2015.

Hirschmann et al., "Upright Cone CT of the hindfoot: Comparison of the non-weight-bearing with the upright weight-bearing Position," Eur Radial. vol. 24, pp. 553-558, 2013.

W. Holub, "4D motion animation of coronary arteries from rotational angiography," Proc. SPIE 7964, Medical Imaging 2011: Visualization, Image-Guided Procedures, and Modeling, pp. 1-10 79641S (Mar. 1, 2011).

* cited by examiner

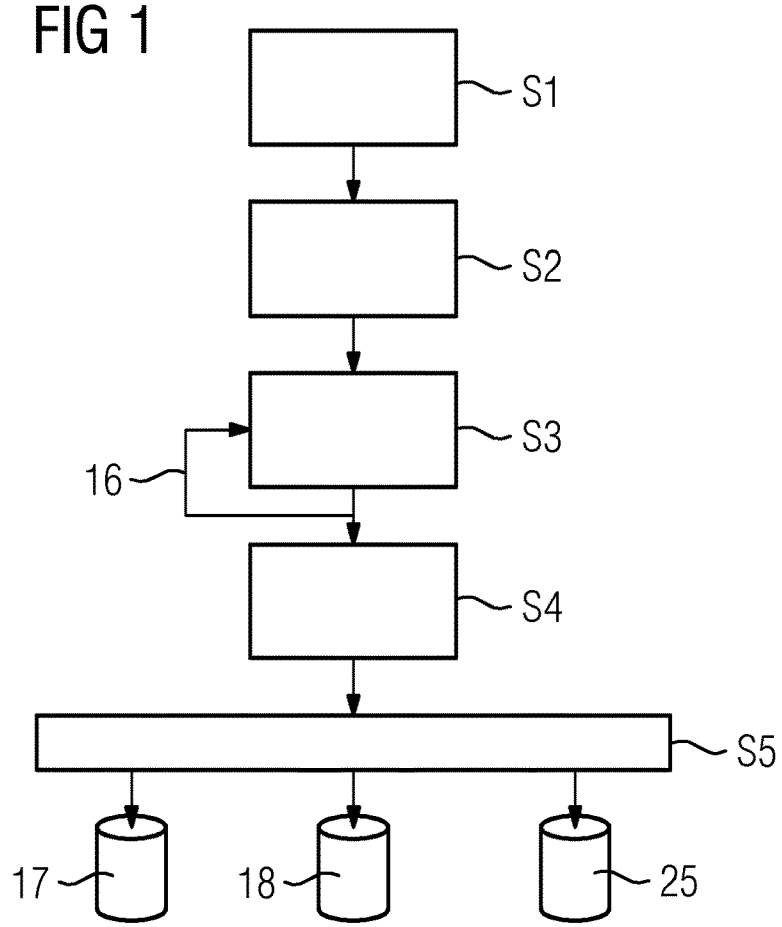
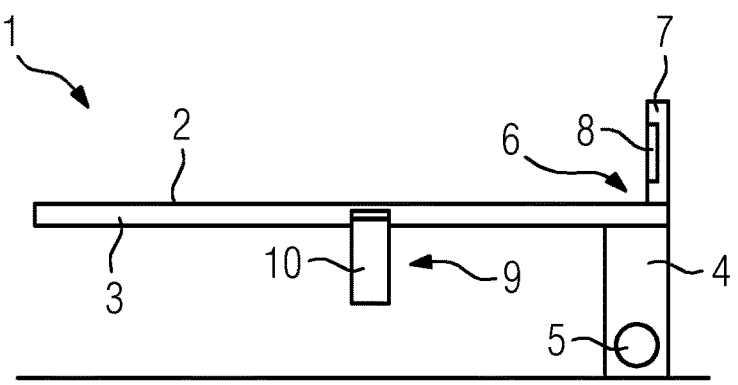

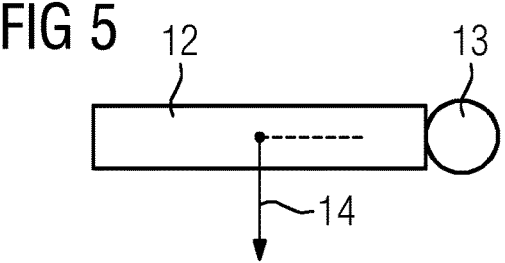
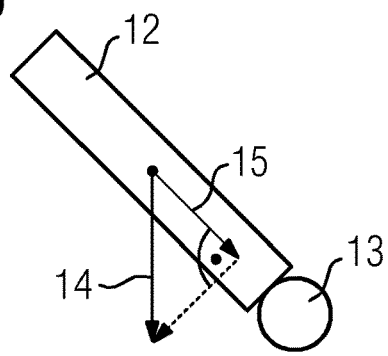
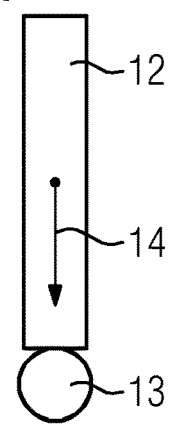

AUTOMATIC DETERMINATION OF JOINT LOAD INFORMATION

The application claims the benefit of German Patent Application No. DE 10 2016 200 202.3, filed Jan. 11, 2016, which is hereby incorporated by reference in its entirety.

TECHNICAL FIELD

The disclosure relates to a method for the automatic determination of at least one joint load information item concerning a joint of a patient, wherein at least one image data set of the loaded joint is recorded by an imaging apparatus. The disclosure additionally relates to an imaging apparatus, such as an X-ray apparatus, a patient couch for such an imaging apparatus, and a computer program.

BACKGROUND

The imaging of joints, (for example of the feet, knees, hips, and spinal column), is well known in the field of medical diagnosis for the purpose of being able to establish the presence of various pathological states. It has also been proposed to record images of such joints in a weight-loaded state, e.g., in order to be able to ascertain musculoskeletal defects. It has been found that joint parameters, such as the distances and orientation of joint components relative to each other differ between a standing position, e.g. a fully loaded position, and a lying position, e.g. an unloaded position. In this connection, see, for example, the article by Anna Hirschmann et al., Eur Radiol (2014) 24:553-558.

The recording of two-dimensional radiography images using an X-ray apparatus in the loaded states of joints is already known in the prior art. Moreover, dedicated imaging apparatuses for the limbs have been proposed which permit 3D imaging of joints of the feet and knees, also with the patient standing, as a loading state. Moreover, new kinds of robot-based X-ray systems have been proposed to allow images of joints over a greater area of the body, for example, including the hips and spinal column.

Three-dimensional imaging in loading states may simplify diagnosis by comparison with 2D imaging. For example, it is possible to record a three-dimensional image data set of a patient lying down (e.g., minimal loading of the joint) and a three-dimensional image data set of a patient standing up (e.g., maximal loading of the joint) using dedicated X-ray systems. However, three-dimensional images in loading states that lie between these extremes are not presently supported by imaging protocols. In the prior art, it has already been proposed to use devices that simulate varying loads in a supine position of the patient. However, it was found that loading of a joint in a supine position does not lead to the same effect as loading of the joint in an upright position.

Another fundamental problem in assessing image data sets of a joint that are recorded in loading states entails, especially in two-dimensional image data sets, the correct extraction of the required information from the image data, since the correct viewing angle and the correct viewing position are not necessarily guaranteed. Moreover, it is difficult to establish correspondences between different loading states.

SUMMARY AND DESCRIPTION

The scope of the present disclosure is defined solely by the appended claims and is not affected to any degree by the statements within this summary. The present embodiments may obviate one or more of the drawbacks or limitations in the related art.

The object of the disclosure is therefore to make available joint information that relates to different loading states and that may be obtained easily and reliably.

To achieve this object in a method of the type described above, provision is made that several image data sets of the joint, of which at least one is three-dimensional, are recorded in each case for different loading states by the imaging apparatus, and, by combined evaluation of the image data sets, the at least one joint load information item is determined.

Therefore, several image data sets are recorded that relate to different loading states of the patient's joint that is to be examined. Of these image data sets, at least one is three-dimensional, since it has been found that a three-dimensional observation of the loading situation in the joint permits much better and more precise viewing in relation to the joint load information. Automatic analysis algorithms are employed in an evaluation unit and advantageously consider the different image data sets at least partly in combination and may thus establish correspondences that allow diagnostically relevant joint load information to be derived, e.g. physical circumstances of interest that may be made the basis of a subsequent diagnosis. Since the complex three-dimensional circumstances may be considered by the analysis algorithms systematically, this provides an extremely reliable basis for analyzing and understanding joints in different loading states. As will be discussed in more detail below, 3D information may be transferred by at least one three-dimensional image data set to optionally present two-dimensional image data sets in order to analyze these automatically, since a more rapid workflow is then achieved with less radiation exposure of the patient. For example, an embodiment is conceivable in which only a single three-dimensional scan is needed, wherein the movement of joint components may then be derived with the change of load from two-dimensional radiography images, a fluoroscopy sequence or tomosynthesis images.

The automatic analysis may take place in three-dimensional space, whereas human observers are limited to two-dimensional cross sections or to multiplanar reformations/projections. The information obtained in three-dimensional space is more accurate and more reliable.

At least one three-dimensional image data set may be recorded at a loading state lying between a lying state in which the joint is under minimal loading and a standing state in which the joint is under maximal loading, and/or in each case at least one image data set may be recorded in the lying state in which the joint is under minimal loading and in the standing state in which the joint is under maximal loading. It is thus expedient, on the one hand, to obtain and therefore record information, therefore an image data set, concerning the lying state in which the joint is under minimal loading and the standing state in which the joint is under maximal loading, so that the extreme points are in each case covered by image data. However, it is expedient if at least one three-dimensional image data set is recorded in an intermediate state between the lying state and the standing state. Thus, for example, improved information concerning the profile of joint parameters may be obtained across the range of possible loads.

For example, a workflow in the context of the method may be one in which the patient is positioned on a patient couch with a tiltable supporting surface. A three-dimensional image data set of the patient is recorded in the lying state, e.g., the supine position of the patient. This first image data set may be a three-dimensional tomographic image data set, a three-dimensional tomosynthesis image data set, and/or a two-dimensional radiography image data set.

The supporting surface is tilted in order to bring the patient to an intermediate state or an intermediate position between lying and standing, so as to record additional image data sets. These additional image data sets may also include three-dimensional tomographic image data sets, three-dimensional tomosynthesis image data sets, and/or two-dimensional radiography image data sets. It is conceivable also to record a series of 2D image data sets, such as a series of fluoroscopy image data sets, while the patient is being tilted from the lying state to the standing state. It is expedient here if the images in the series of 2D image data sets are recorded in the same recording geometry in respect of a patient coordinates system but in different recording geometries in respect of the world coordinates system.

A further recording variant that is conceivable is also to record two-dimensional image data sets during a movement of the patient, e.g., from the lying state to the standing state, and join these together to form a three-dimensional combination data set obtained, e.g., by reconstruction. For example, if twenty (20) seconds are needed to move the patient from the lying position to the standing position, a multiplicity of two-dimensional image data sets of different recording geometry may be recorded during this time period, and from these it is then possible to form, (e.g., by reconstruction), a three-dimensional image data set as combination data set. If the imaging apparatus is an X-ray apparatus, projection images may be recorded along a recording trajectory defined with respect to the patient, (for example, along a circular path or partial circular path), from which a three-dimensional combination data set may in principle be determined by iterative reconstruction and/or filtered back-projection.

However, a direct reconstruction of such an image data set would lead to artefacts, since movement occurs through the change in loading. Therefore, an expedient refinement is one in which an algorithm of the model-based reconstruction is used to determine the combination data set. Such reconstruction methods are in principle already known and were created for cases in which movement may not be avoided, for example, in the reconstruction of coronary arteries in the area of the moving heart; see, for example, the conference paper by W. Holub, "4D motion animation of coronary arteries from rotational angiography", Proc. SPIE 7964, Medical Imaging 2011: Visualization, Image-Guided Procedures, and Modeling, 79641S (Mar. 1, 2011); doi:10.1117/12.877969. This has also already been employed in other problematic areas, for example, in the reconstruction of contrast agent flow. Such algorithms may now also advantageously be used in the context of the present disclosure and have the advantage of already containing information concerning the change of loading (e.g., concerning the movement during the recording procedure). By using such methods, a four-dimensional movement data set, which will be discussed in more detail below, may also be determined.

When the patient is finally in the standing position, with the joint therefore in the standing loading state, an image data set is again recorded. This image data set may once again be a three-dimensional tomographic image, a three-dimensional tomosynthesis image data set, and/or a two-dimensional radiography image data set.

Therefore, in an advantageous embodiment, provision is made that, in order to set different loading states, a patient couch tiltable about a rotation axis is used in such a way that the patient is movable, by the tilting of the patient couch, between a lying state in which the joint is under minimal loading and a standing state in which the joint is under maximal loading. The patient couch therefore has a supporting surface for the patient, which supporting surface is tiltable so that different loading states may be adopted for the joint while the patient is transferred from a lying position to a standing position. Patient couches with tiltable supporting surfaces for the patient are already known and may be used in the context of the present disclosure.

However, in an advantageous embodiment, a patient couch is used having a rotation axis arranged particularly close to the floor at an end of the supporting surface to which the feet are intended to point, e.g. at a foot-side end of the supporting surface. In this embodiment, the disclosure thus proposes a novel patient couch design that permits more room under the patient table as it rotates. For this purpose, the rotation axis for the tilting between the standing position and the lying position is provided at the foot-side end of the supporting surface, e.g. at the end where the patient's feet are positioned. This rotation axis is may be secured to the floor and arranged near the floor. In this way, more flexible imaging is permitted such that, for example, projection data for a three-dimensional reconstruction may be recorded by X-ray systems while the patient couch, specifically the supporting surface, is tilted.

In an expedient refinement of this embodiment, the patient couch is designed in such a way that the foot-side end of the supporting surface terminates with a foot plate that is perpendicular to the supporting surface and that offers a foot rest. In this way, the patient couch used also has a foot support that has no effect in the horizontal position of the patient couch but is needed when the supporting surface is pivoted to the vertical position, since the patient is then able to stand with his or her feet on the foot plate.

A pressure sensor may be arranged on the foot plate, wherein a pressure value measured by the pressure sensor at the time of the recording of an image data set is assigned to the image data set, stored, and taken into consideration in the evaluation. For example, the foot plate may therefore have a pressure plate on which the patient's feet are positioned such that, upon tilting of the supporting surface, a pressure acting on the foot plate, and therefore on the pressure plate, may be measured. Such a pressure value gives a clear indication of the loading to which the joint was exposed while an image data set is recorded. Models may also be accepted in which the actual loading of the joint is able to be quantified from the pressure value. Such a pressure value therefore provides useful and helpful information that may be taken into consideration when evaluating the image data sets during the biomechanical analysis of the image data. It is possible for the image data sets that were recorded in intermediate positions or in intermediate states to be correlated not only with the tilting angle but alternatively, or additionally, with the pressure value.

It is moreover expedient if a retaining device, (e.g., a retaining device such as a strap), is arranged on the patient couch and is used to hold the patient during the tilting about the rotation axis. For example, a safety strap may thus be used as a retaining device in order to increase patient safety during the tilting of the patient couch. In an expedient refinement, an X-ray apparatus is used as the imaging apparatus. On account of its contrasts, X-ray imaging is suitable for providing clear images and resolutions of various components of a joint, bones, and/or cartilage structures.

However, other imaging techniques may in principle also be used, for example, magnetic resonance imaging and/or ultrasound imaging.

In a refinement of the disclosure in this context, provision is made that an imaging device belonging to the X-ray apparatus and including an X-ray detector and an X-ray emitter is mounted on at least one robot device and, by the latter, is moved to imaging positions assigned to loading states. The X-ray apparatus may be robot-based, such that image data sets may also be recorded with the patient couch tilted to intermediate positions. For example, an X-ray apparatus with a C-arm mounted on a robot may be used. Of course, it is also conceivable to use other apparatuses, for example, the "Multitom Rax" radiography system recently brought onto the market by Siemens Healthcare GmbH.

In a first embodiment of useful joint load information, provision may be made that a four-dimensional movement data set of the joint is determined as joint load information from the image data sets, wherein the loading is used as a fourth dimension in addition to the three spatial dimensions. A four-dimensional movement data set of this kind may be displayed to a user and constitutes a very useful tool for a subsequent diagnosis, in connection with further joint load information items. The four-dimensional movement data set thus corresponds to a sequence of three-dimensional images under variable loading. As the loading changes, correlations and changes may be derived from a four-dimensional movement data set of this kind.

In this context, it is expedient if, in order to generate the movement data set, three-dimensional image data sets of different loading states and/or three-dimensional intermediate data sets derived from image data sets of different loading states are interlinked and/or, by interpolation between different loading states, are connected to form a load-continuous movement data set. It is therefore conceivable that a number of three-dimensional image data sets that were recorded under different loading conditions are combined by simple interlinking to form the four-dimensional movement data set. However, it is also possible, by interpolation, to obtain further information for indirectly recorded loading states that lie between recorded loading states.

For this purpose, provision may expediently be made that the interpolation takes place in respect of movement parameters that describe movements between different loading states. The interpolation therefore does not take place on a gray-scale value plane between image data sets but instead may be in movement parameters that describe the movement between different loading states. The movement parameters may in this case be defined in a movement model of different joint components segmented by segmentation in the image data sets. The set-up of a movement model may also already be part of the determination of further joint load information items, since a multiplicity of variables for the behavior of the joint during loading follow from such a movement model and also already from the segmentation of individual joint components, as will also be set out in more detail below.

In an embodiment, provision is made that, if only a two-dimensional image data set is available for a movement state, three-dimensional movement information items with respect to a loading state, for which a three-dimensional image data set is available, may be determined by rigid 3D-2D registration and are used to generate an intermediate data set. For example, if some of the image data sets are two-dimensional, for example, in the case of radiography image data sets, or if the three-dimensional information of the image data set is not sufficiently reliable, (for example in tomosynthesis image data sets), it is possible to exploit the fact that reliable three-dimensional information is present at least in one image data set. In the at least one three-dimensional image data set, joint components may be segmented and/or landmarks may be determined, which permits 3D-2D registration for the lower-dimensional image data sets. From this, it is in turn possible to infer the movement of the joint components as the loading changes. Given that joint components may be rigid, a rigid registration is sufficient, as a result of which the movement components also arise in dimensions perpendicular to the image plane of the two-dimensional image data sets. Specifically, provision may be made, for example, that the segmentation of joint components in the at least one three-dimensional image data set is changed on account of the registration parameters that describe the transformation, so as to obtain an intermediate data set as part or for determination of the four-dimensional movement data set.

It is also possible, as has been explained above, that information concerning the fourth dimension are obtained from model-based reconstructions. In this case, during a movement of the patient between two loading states, (e.g., from the lying state to the standing state), two-dimensional image data sets, (e.g., X-ray projection images), are recorded in different recording geometries with respect to the patient. Using an algorithm of the model-based reconstruction reproducing the movement taking place in the joint on account of the change of loading, a three-dimensional image data set (e.g., combination data set) for initially one loading state (for example the lying state or the standing state) may be reconstructed free of movement artefacts and constitutes an image data set that is to be evaluated in order to determine the joint load information. However, the information obtained in the movement model of the algorithm for the model-based reconstruction may be used to determine the four-dimensional movement data set, or joint parameters and load parameters are also determined as joint load information, as are discussed below.

As has already been indicated, in an embodiment, joint parameters and loading parameters may also be determined as joint load information, specifically at least one joint parameter describing the geometry of the joint for several loading states, and/or at least one loading parameter describing the profile of such a joint parameter with the loading. For example, a shortest distance between at least two joint components of the joint, between two bones and/or cartilage structures, and/or an opening angle between at least two joint components of the joint may be determined as a joint parameter. Such measurements of spaces, (e.g., intervertebral spaces and other joint spaces), may help an investigator in a diagnosis to characterize degenerative processes that may cause pain. For example, cartilage erosion, osteophytes, and incorrect orientation of the bones lead to narrowing of joint spaces. Since, in the case of the knee, the bone/cartilage interfaces of tibia, femur, and patella have complex curvatures with protruding and recessed areas, the measurement of free joint spaces in two-dimensional representations, for example, two-dimensional radiography image data sets, is extremely complicated and, above all, imprecise, since the distances to be seen in these do not correspond exactly to the real distances in three-dimensional space. However, since the present disclosure operates with at least one three-dimensional image data set and uses automatic analysis algorithms, significant improvements may be achieved here.

Specifically, provision may be made that, in order to determine at least one joint parameter for a loading state, at least one landmark of at least one joint component in the image data set assigned to the loading state is identified and located, wherein the localization information is included in the determination of the joint parameter. For example, distinctive points, for example condyles and/or outermost points of bones and/or cartilage structures, may be chosen as landmarks and accordingly located. Even today, such landmarks are often used in the prior art in order to be able to define certain joint parameters, for example, an angle between a straight line defined by the outermost lateral end points of the patella and a straight line defined by the two protruding parts of the tibia or of the femur. Therefore, straight lines connecting two anatomical landmarks may be determined and defined, wherein the joint parameters follow from the lines themselves or from the relationship to other such lines.

It is however conceivable that the surface of at least one joint component is determined by segmentation, wherein the joint parameter is determined via the spatial relationship of surfaces of different joint components and/or of one surface of a joint component to a landmark of another joint component. For example, two different bone surfaces may be segmented and the two points of shortest distance on both surfaces may be detected. For example, it is thus possible, for measurement of the medial compartment, to calculate the bone interspace between the distal convex margins of the condyle of the femur and the medial tibial plateau.

Provision may be made that in order to identify and locate at least one landmark, a landmark algorithm trained by machine learning is used. Specifically, provision may be made that a training data set is used in which the necessary landmarks are marked in a set of training images. A machine-learning landmark algorithm is trained on the basis of these training data to detect and locate the landmarks. In a specific embodiment, provision may be made for this purpose that a support vector machine and/or a neuronal network and/or a random forest is used as landmark algorithm and/or, in order to test a trained landmark algorithm, a cross-validation method and/or a test data set independent of the training data is used. In the cross-validation method, the training data are divided into two parts, wherein, for example, 90% of the training data are used for training the landmark algorithm, and 10% of the training data are used to check it. This process may be repeated several times with new allocation of training data for the training/checking. As has been mentioned, however, independent additional test data in which the landmarks are marked are also conceivable.

In an embodiment, a joint model is determined on the basis of landmarks and/or surfaces and/or joint parameters determined in three-dimensional image data sets, wherein, for two-dimensional image data sets, the joint parameter in an instance of the joint model configured to the loading state of the two-dimensional image data set is determined by identification of at least one feature, imaged in the model, in the two-dimensional image data set and by comparison of identified features of the joint components. As has already been indicated in respect of the four-dimensional movement data set, it is possible to use 3D information in a three-dimensional image data set to draw conclusions regarding the relationships in two-dimensional image data sets in other loading states, for example, in the context of 3D-2D registration. In order to establish the link, it is possible to use the segmented joint components or segmented landmarks that ought to be seen in all image data sets. If suitable and corresponding features were found, conclusions may be drawn regarding the movement that has taken place between the loading states, e.g., in view of the fact that joint components may be rigid. If the joint components are finally combined as a joint model, mainly their positions and orientations ultimately change between different loading states, which may be described by rigid transformations that may also be readily estimated from two-dimensional image data sets. Finally, therefore, landmarks/surfaces/joint parameters that were initially found or determined in a three-dimensional image data set may also be found for all other image data sets by registration processes, e.g., based on a movement model. Even when using two-dimensional image data sets, this allows the load-related changes of the joint geometry, (e.g., of joint spaces), to be calculated and displayed to the user.

In an embodiment, provision is therefore made that base joint parameters are initially determined for a specific loading state, such as the state of least loading, in a three-dimensional image data set, and, by locating feature correspondences in the image data sets for other loading states, (e.g., by a registration process), the joint parameters for the other loading states are derived from the base joint parameters. The loading state of least loading, (e.g., the lying state), is recommended as a loading state to be considered initially, since here the distances between joint components may be at their greatest. Using at least one joint parameter, a visualization of the image data set may expediently be configured. For example, in a specific embodiment, it is possible that a visualization of the image data set is configured. For example, in a specific embodiment, it is possible that a plane for a multiplanar reformation (MPR) and/or parameters of a three-dimensionally rendered presentation are determined based on at least one point defined by at least one joint parameter and/or at least one line and/or surface defined by at least one joint parameter. It may be in this connection if the plane for the multiplanar reformation is defined such that a line marking the shortest distance between two joint components lies in it. The intersection plane of the multiplanar reformation is therefore constructed such that a line marking the shortest distance between two joint components lies in it. Thus, a view of this shortest distance is offered. In this connection, it is expedient if, in order to establish the degrees of freedom of the plane existing beside the line marking the shortest distance, the plane is chosen such that it lies as close as possible to a sagittal and/or coronal and/or axial plane of the body. The construction of the intersection plane of the MPR may thus be continued such that it lies as close as possible to MPR planes that may be used to determine joint spaces for this specific anatomical area.

The sections of the new MPR that are thus determined are presented to the user, e.g., with the distance line highlighted. The user is then able to scroll through the sections whose planes lie parallel to the plane with the distance line. Alternatively, the presentation may also be rotated about the distance line.

However, presentations may also be optimized in the area of rendering, such that an optimal view is afforded of narrowed areas of the joint. For example, in the rendering of a presentation, the lighting mode may be chosen such that the closest distance between joint components is emphasized/illuminated. The viewpoint may be chosen within the joint or automatically outside the joint so that the narrowest joint space is optimally visualized.

It may thus be stated that, in the visualization, the property described by the joint parameters is emphasized and/or marked, and/or the visualization is modified in reaction to at least one user input. Possible ways of modifying a visualization of a rendered presentation are already known and may also be used in the context of the present disclosure.

Besides the method, the disclosure also relates to an imaging apparatus, such as an X-ray apparatus, designed for carrying out the method. All of the statements concerning the method may be transposed analogously to the imaging apparatus. The imaging apparatus may thus have a control system that has a recording unit which controls the recording apparatus and may also control the patient couch in such a way that the image data sets that show the joint in different loading states are obtained. An evaluation unit may perform the analysis of the image data sets for determination of the joint load information and may likewise form part of the control system.

The disclosure further relates to a patient couch for an imaging apparatus, for setting different loading states of a joint of a patient, the patient couch having a supporting surface for the patient tiltable about a rotation axis in such a way that the patient is movable, by the tilting of the patient couch, between a lying state in which the joint is under minimal loading and a standing state in which the joint is under maximal loading, which is distinguished in that the patient couch has a rotation axis that is arranged particularly close to the floor at a foot-side end of the supporting surface. The rotation axis may be secured on the floor. All of the statements made above may also be transposed to the patient couch. Therefore, the patient couch may have a foot plate that adjoins the foot-side end of the supporting surface, lies perpendicular to the supporting surface and offers a foot rest, which may advantageously include a pressure sensor that is able to measure a pressure value at the time of the recording of an image data set. Moreover, a retaining device, such as a retaining device like a strap, may be arranged on the patient couch and holds the patient during the tilting about the rotation axis.

Finally, the disclosure also relates to a computer program that performs the acts of the method when run on a computing device. The computer program may be stored on an electronically readable data carrier, such as a non-transient data carrier such as a CD-ROM. The computing device may be the control system of the X-ray apparatus. The statements made above also apply analogously to the computer program.

BRIEF DESCRIPTION OF THE DRAWINGS

Further advantages and details of the present disclosure will become clear from the illustrative embodiments described below and from the drawing, in which:

FIG. 1 depicts a flow diagram of an illustrative embodiment of the method.

FIG. 2 depicts an example of a patient couch.

FIGS. 5 to 7 depict explanatory diagrams of different loading states.

DETAILED DESCRIPTION

Figure 3:
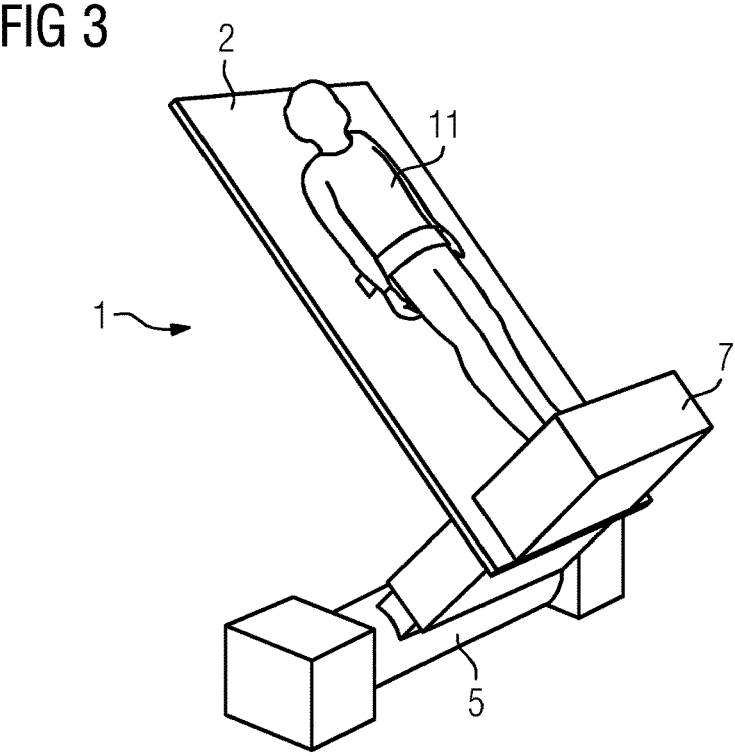
FIGS. 3 and 4 depict examples of the patient couch in further settings.

FIG. 1 depicts a flow diagram of an illustrative embodiment of the method for determination of joint load information. In an act S1, a patient to be examined is placed on a patient couch of an imaging apparatus, here an X-ray apparatus, which permits a wide variety of robot-based settings of the recording device.

A patient couch 1 that may be used here is explained in more detail with reference to FIGS. 2 to 4.

FIG. 2 depicts a schematic sketch of the patient couch 1. The patient couch 1 has a patient table 3 with a supporting surface 2 on which the patient to be examined may be placed. The patient table 3 is carried by a stand 4, wherein it is moreover tiltable about a rotation axis 5 close to the floor, here mounted on the floor. The rotation axis 5 is arranged at the foot-side end 6 of the supporting surface 2.

At the foot-side end of the supporting surface 2, the latter is moreover terminated by a foot plate 7, which extends perpendicularly with respect to the supporting surface 2 and has a pressure sensor 8 via which pressure values may be recorded in different tilting positions of the patient couch 1. To increase patient safety, a retaining device 9 in the form of a safety strap 10 is moreover provided.

In act S1 of the method, the patient is now placed in a supine position on the supporting surface 2 such that the flats of the feet rest on the foot plate 7. In the lying position, the loading of a joint to be examined, (e.g., the knee joint), is minimal. If the supporting surface 2 is now tilted about the rotation axis 5, the weight that the joint has to support increases, and so too does the load, as the tilt angle increases. FIGS. 3 and 4 show by way of example, and once again schematically, the patient couch 1 in two further tilting positions with a patient 11 arranged thereon. FIG. 3 depicts a 45° tilting position and FIG. 4 depicts a 90° tilting position. In the case of FIG. 4, the patient 11 stands on the foot plate 7, such that a standing position is obtained in which a maximal load acts on the joint.

This is explained again in more detail with reference to FIGS. 5 to 7. FIG. 5 illustrates the lying state, in which the trunk 12 and the joint 13 of the patient 11, here the knee joint, are shown in abstract form. The arrow 14 symbolizes the force of gravity of the trunk 12. Since there is evidently an angle of 90° between the force of gravity and the arrangement of the joint 13, there is no load acting on the joint 13.

Figure 4:
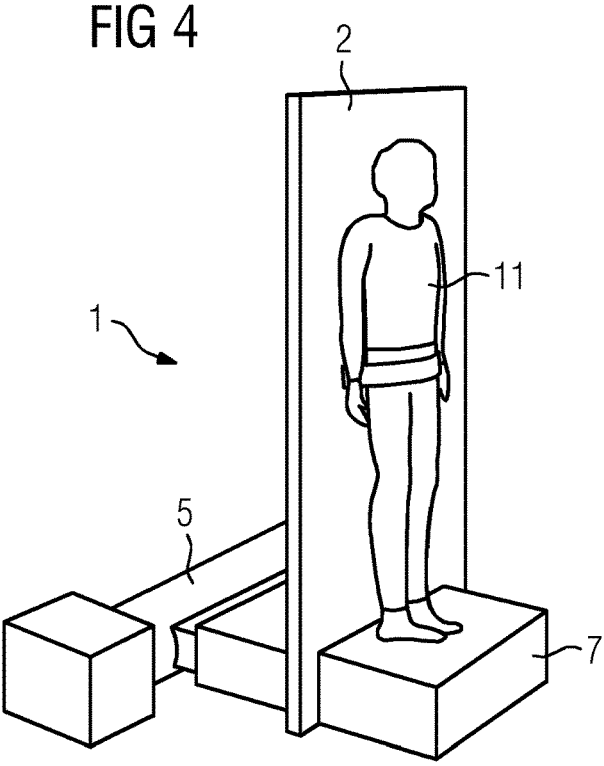

FIG. 6 depicts an intermediate state in which the patient 11 is tilted through 45° (corresponding to FIG. 3). An effective weight, symbolized by an arrow 15, which forms a proportion of the weight of the trunk 12, now acts on the joint 13. FIG. 7 depicts the other extreme, namely the standing position (corresponding to FIG. 4), in which said weight of the trunk 12 acts completely on the joint 13. The effective force loading the joint 13 may thus be estimated in simplified form as: $F_{eff} = m_{trunk} \cdot g_0 \cdot \cos(\alpha)$, wherein: $g_0$ is the gravitational constant, m is the mass, and α is the angle between the force of gravity and the orientation of the patient 11.

Given the use of robots and/or telescopic arms in the X-ray apparatus employed, there are many degrees of freedom of movement for the imaging device, such that image data sets of the joint 13 may be recorded in a very wide variety of loading states.

The method as per FIG. 1 is continued in an act S2 in which a three-dimensional image data set of the joint 13 of the patient 11 is now recorded in the lying position, such that the load state corresponds to the lying state (cf. FIG. 5).

In an act S3, a further, two-dimensional or again a three-dimensional image data set of the joint 13 is recorded, wherein the patient 11 is brought automatically by the tiltable patient couch 1 to an intermediate state between the lying state and the standing state. This means there is partial loading of the joint 13. As is indicated by the arrow 16, it is of course also possible to record several image data sets in such intermediate positions.

In an act S4, the standing position (cf. FIG. 7) is reached, where a final, three-dimensional image data set is recorded.

After the acts S2 to S4, a plurality of image data sets for different loading states of the patient 11 are therefore available, wherein at least one three-dimensional image data set for the lying state and one for the standing state are present as loading state.

In an act S5, at least one joint load information item is now intended to be automatically extracted from these image data sets by analysis algorithms. The first recorded, three-dimensional image data set, obtained in the lying position, may be used in order to identify the individual joint components of the joint 13 based on landmarks and/or segmentation processes and to at least implicitly determine their position and orientation. These joint components may be used to form a joint model as a basis of a movement model for the movements taking place during the load changes. It has been found that the joint geometry is at its most open in the lying state, which means that the distances between the individual joint components are at their greatest, such that segmentation/locating of landmarks is simple. When the joint components are identified in one image data set, they may also be easily located in the other image data sets, for example, based on feature correspondences or suitable start values for segmentation/landmark detection there. Since joint components, (e.g., bones and/or cartilage structures), may be rigid, it is also possible, for two-dimensional image data sets, to reproduce the corresponding joint geometries three-dimensionally in the movement model by 3D-2D registration processes.

With regard to landmark detection, a landmark algorithm trained by machine learning is used.

An intermediate result of the act S5 is therefore that the positions of landmarks/surfaces of joint components or at least the orientation and position of joint components are known for all the loading states for which image data sets were recorded. In the case of two-dimensional image data sets, a three-dimensional intermediate data set may also be generated using the knowledge from the three-dimensional image data sets. A multiplicity of joint load information items may now be derived from this intermediate result.

A four-dimensional movement data set 17 as joint load information item is shown symbolically and by way of example in FIG. 1. Here, the loading forms the fourth dimension in addition to the three spatial dimensions. The four-dimensional movement data set may, on the one hand, be generated by simple interlinking of image data sets/intermediate data sets of different loading states; it is also possible to interpolate between the different loading states in order to obtain a load-continuous movement data set. The interpolation is made in respect of movement parameters describing movements in the movement model, e.g., in each case relative to defined joint components.

The joint load information items 18 further shown symbolically in FIG. 1 concern joint parameters, which describe the geometry of the joint 13, for different loading states and the profile of such joint parameters with loading parameters that describe the loading. Examples of joint parameters in defined loading states, which describe the geometry of joints 13, are explained in more detail with reference to FIGS. 8 and 9.

Figure 8:
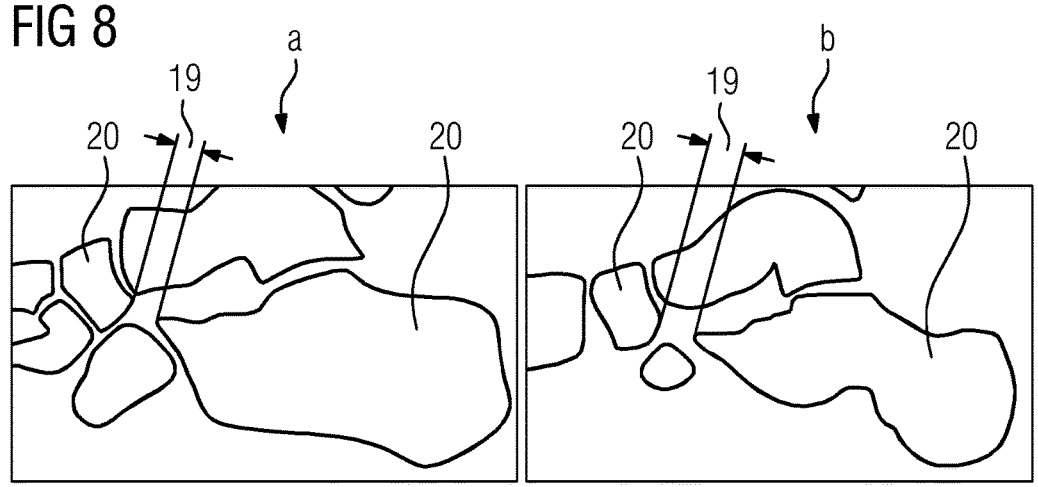
FIG. 8 depicts a diagram of the determination of a first joint parameter.

FIG. 8 concerns the determination of a joint space, with image a on the left having been recorded under greater loading than image b on the right. The minimum distance 19 between the joint components 20 is intended to be determined as a joint parameter. As may be seen (see image b on the right), the distance 19 becomes greater as the loading decreases.

The minimum distance 19 may easily be determined in three dimensions, if the surfaces of the joint components 20 are known, using a suitable analysis algorithm.

Figure 9:
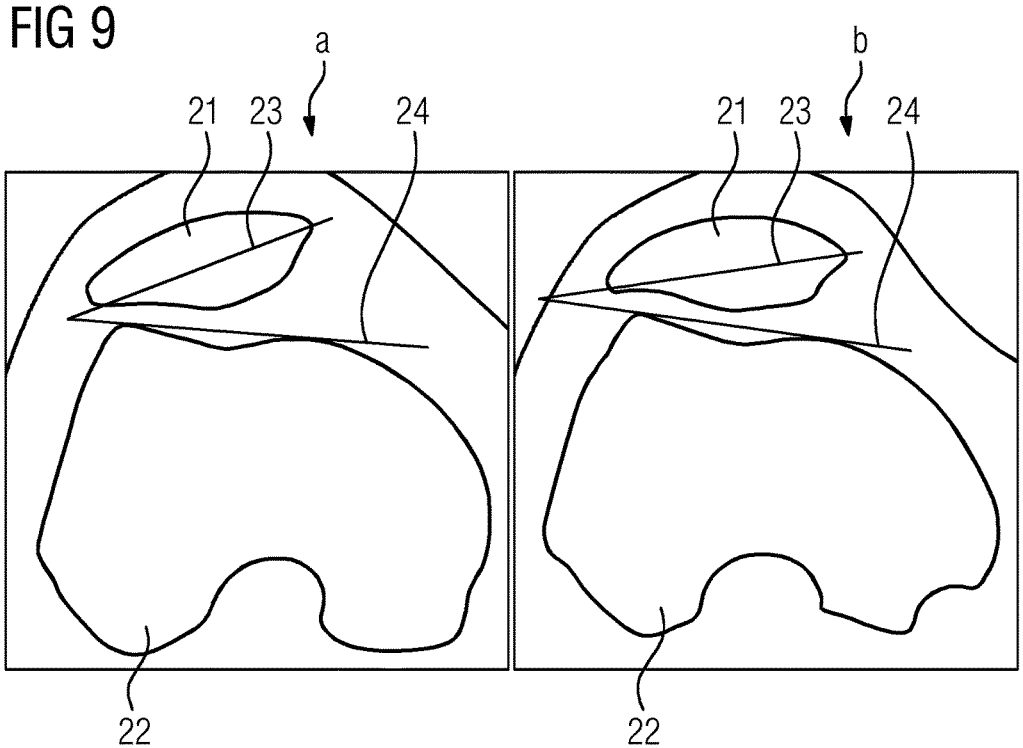
FIG. 9 depicts a diagram of the determination of a second joint parameter.

FIG. 9 depicts a further example, in this case in relation to a knee joint, of which the patella 21 and femur 22 are shown. The laterally outer points of the patella 21 as landmarks define the straight line 23, while the forwardly curved areas of the condyle of the femur 22 as landmarks define the straight line 24. The angle between these two straight lines is intended to be determined as a joint parameter. Since the loading is less in image a on the left than it is in image b on the right, it is clear that the angle increases as the loading decreases.

If such joint parameters are therefore considered across different loading states, therefore for different loads, it is also possible to determine load parameters that quantify the physical circumstances during loading.

Joint parameters and load parameters may also be used to assist users with suitable visualizations, as symbolized schematically in FIG. 1 by the joint load information item 25.

For example, a plane for a multiplanar reformation (MPR) to be newly generated may be defined such that the line of shortest distance (cf. FIG. 8) lies in it and at the same time is as close as possible to classical planes for the MPR, e.g., an axial, coronal, or sagittal plane. In such MPR sections, the shortest distance may be shown highlighted or overlaid. However, it is also possible to use joint parameters and the recorded image data to optimize visualizations of these joint parameters, which are based on rendered presentations, in order to see the properties that the joint parameters describe. Irrespective of the nature of the visualization, the user is of course afforded possibilities of manipulating the presentations, for example, scrolling through the MPR sections, in order to rotate the shortest distance or, in rendered presentations, to adapt the viewing angle, the illumination, and the like.

For example, presentations such as in FIG. 8 and FIG. 9 with suitably visualized joint parameters may be provided as MPR sections.

In a subsequent act not belonging to the method, the joint load information items 17, 18, and 25 obtained may be used to make a diagnosis.

Figure 10:
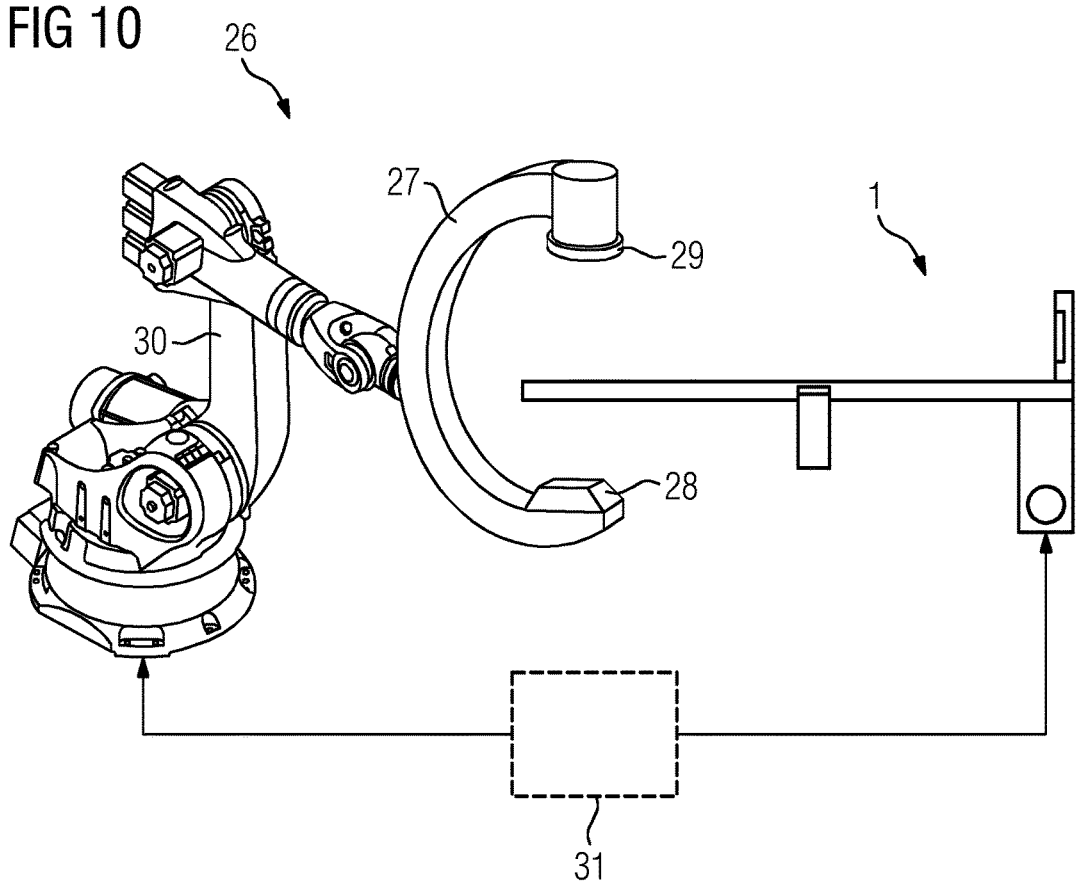
FIG. 10 depicts an imaging apparatus according to a first embodiment.

FIG. 10 finally depicts a schematic sketch of a first imaging apparatus 26, here an X-ray apparatus. In addition to the patient couch 1 already described, the imaging apparatus 26 has a C-arm 27 on which an X-ray emitter 28 and an X-ray detector 29 are arranged opposite each other. The C-arm 27 is carried by a robot arm 30 in order to allow image data sets to be recorded in different loading states. A control system 31, only symbolized here, is configured to carry out the method.

Alternative embodiments of the imaging apparatus are also conceivable, for example, those sold by Siemens Healthcare GmbH under the name "Multitom Rax".

Figure 11:
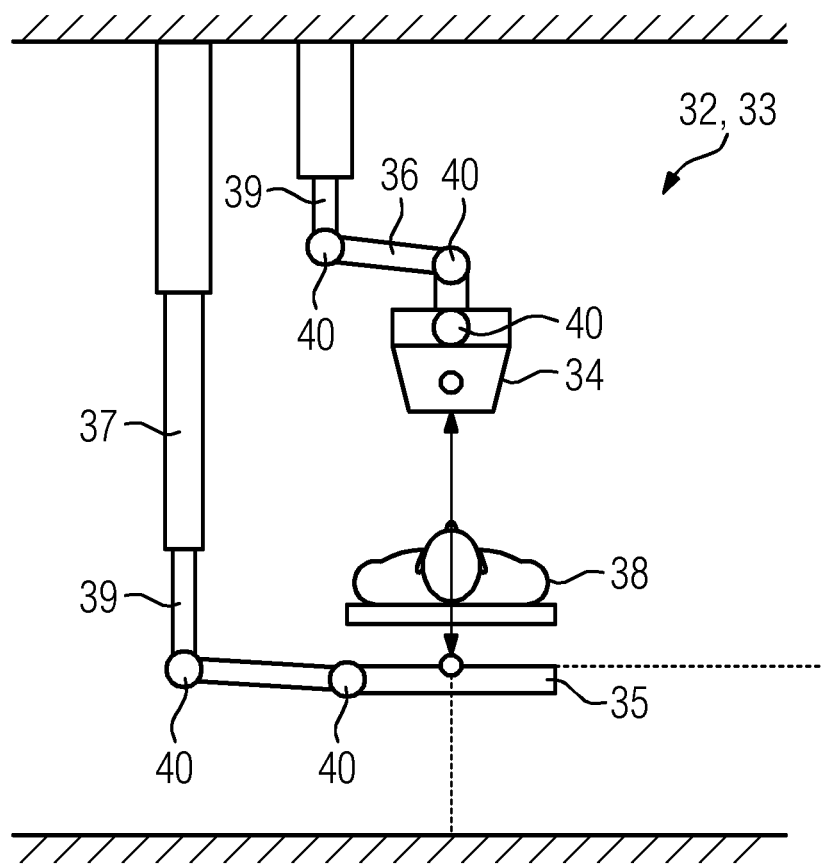
FIG. 11 depicts an imaging apparatus according to a second embodiment.

Accordingly, FIG. 11 depicts a second embodiment of an imaging apparatus 32 in the form of an X-ray apparatus 33. The latter has an X-ray emitter 34 and an X-ray detector 35, which are each secured on brackets 36, 37 to the ceiling. A patient 38 may be arranged between the X-ray emitter 34 and the X-ray detector 35. The recording device may be set in a large number of degrees of freedom via telescopic arms 39 and articulations 40. The control system of the X-ray apparatus 33 is configured to carry out the method.

A computer program (also known as a program, software, software application, script, or code) can be written in any form of programming language, including compiled or interpreted languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Processors suitable for the execution of a computer program include, by way of example, both general and special purpose microprocessors, and any one or more processors of any kind of digital computer. Generally, a processor receives instructions and data from a read only memory or a random access memory or both. The essential elements of a computer are a processor for performing instructions and one or more memory devices for storing instructions and data. Generally, a computer also includes, or is operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non-volatile memory, media and memory devices, including by way of example semiconductor memory devices, e.g., E PROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

Although the disclosure has been more specifically set out and described in detail based on the illustrative embodiment, the disclosure is not restricted by the disclosed examples, and other variations may be derived from these by a person skilled in the art, without departing from the scope of protection of the disclosure.

The invention claimed is:

1. A method for automatic determination of at least one joint load information item concerning a joint of a patient, the method comprising:

recording a plurality of image data sets of the joint for different loading states by an imaging apparatus, wherein the plurality of image data sets comprises at least one three-dimensional image data set for at least one loading state;

reconstructing, using a model-based reconstruction algorithm reproducing a movement taking place on the joint between the different loading states, a three-dimensional combination image data set free of movement artefacts; and determining, by an evaluation of the three-dimensional combination image data set, the at least one joint load information item, wherein the at least one joint load information item comprises a four-dimensional movement data set of the joint, wherein a loading is used as a fourth dimension in addition to three spatial dimensions, wherein the loading varies according to a movement of the patient, and wherein a change in the four-dimensional movement data set of the joint corresponds to a change in the loading.

2. The method of claim 1, wherein the recording of the at least one three-dimensional image data set comprises a recording in a loading state positioned between a lying state in which the joint is under minimal loading and a standing state in which the joint is under maximal loading, and/or wherein the recording of the plurality of image data sets comprises a recording in the lying state in which the joint is under minimal loading and a recording in the standing state in which the joint is under maximal loading.

3. The method of claim 1, further comprising:

setting the different loading states by tilting of a patient couch about a rotation axis to move the patient between a lying state in which the joint is under minimal loading and a standing state in which the joint is under maximal loading.

4. The method of claim 3, further comprising:

positioning the rotation axis of the patient couch close to a floor at a foot-side end of a supporting surface to which feet of the patient are configured to point.

5. The method of claim 4, wherein the patient couch is configured such that the foot-side end of the supporting surface terminates with a foot plate, which is perpendicular to the supporting surface and includes a foot rest, wherein a pressure sensor is arranged on the foot plate; and wherein a pressure value measured by the pressure sensor at a time of the recording of the plurality of image data sets is assigned to the respective image data set, stored, and taken into consideration in the evaluation.

6. The method of claim 1, wherein, in order to generate the four-dimensional movement data set, the plurality of image data sets for the different loading states and/or three-dimensional intermediate data sets derived from the plurality of image data sets for the different loading states are interlinked, connected by interpolation between the different loading states, or interlinked and connected to form a load-continuous movement data set.

7. The method of claim 6, wherein, when at least one two-dimensional image data set is available for a loading state during the movement of the patient, each three-dimensional image data set of the plurality of image data sets for the different loading states comprises three-dimensional movement information items with respect to each loading state, and wherein the three-dimensional movement information items are determined by rigid 3D-2D registration and are used to generate the three-dimensional intermediate data sets.

8. The method of claim 1, wherein, during the movement of the patient between two loading states, two-dimensional image data sets are recorded in different recording geometries with respect to the patient, and the four-dimensional movement data set is reconstructed using an algorithm of a model-based reconstruction.

9. The method of claim 8, wherein the two loading states are a lying state and a standing state.

10. The method of claim 8, wherein the two-dimensional image data sets are X-ray projection images.

11. The method of claim 1, wherein the determining of the at least one joint load information item comprises: determining at least one joint parameter describing a geometry of the joint for the different loading states, determining at least one loading parameter describing a profile of the at least one joint parameter with the loading, or a combination thereof.

12. The method of claim 11, further comprising:
determining, as the at least one joint parameter, a shortest distance between at least two joint components of the joint; and/or
determining an opening angle between the at least two joint components of the joint.

13. The method of claim 12, wherein the at least two joint components comprise bones, cartilage structures, or both the bones and the cartilage structures.

14. The method of claim 11, wherein, in order to determine the at least one joint parameter for the different loading states:
(1) at least one landmark of at least one joint component in the plurality of image data sets assigned to the different loading states is identified and located, wherein localization information is included in the determination of the at least one joint parameter, and/or
(2) a surface of the at least one joint component is determined by segmentation, wherein the at least one joint parameter is determined via a spatial relationship of surfaces of different joint components, of one surface of a joint component to at least one landmark of another joint component, or a combination thereof.

15. The method of claim 14, further comprising:
determining a joint model based on landmarks, surfaces, joint parameters, or any combination thereof, determined in the at least one three-dimensional image data set,
wherein, for a two-dimensional image data set, the at least one joint parameter of the at least one joint component in an instance of the joint model configured to a loading state of the two-dimensional image data set is determined by identification of features, imaged in the model, in the two-dimensional image data set and by comparison of the identified features.

16. The method of claim 11, the method further comprising:
determining base joint parameters for the at least one loading state, in the at least one three-dimensional image data set; and
deriving the joint parameters for other loading states from the base joint parameters by locating feature correspondences in the image data sets for the other loading states.

17. The method of claim 16, wherein the feature correspondences are located by a registration process.

18. The method of claim 11, wherein a visualization of the at least one three-dimensional image data set is configured using the at least one joint parameter.

19. The method of claim 18, the method further comprising:
determining a plane for a multiplanar reformation, parameters of a three-dimensionally rendered presentation, or the plane for a multiplanar reformation and the parameters of the three-dimensionally rendered presentation based on at least one point defined by the at least one joint parameter, at least one line defined by the at least one joint parameter, the surface defined by the at least one joint parameter, or any combination thereof.

20. An imaging apparatus comprising:
a recording unit configured to record a plurality of image data sets of a joint of a patient for different loading states by an imaging apparatus, wherein the plurality of image data sets comprises at least one three-dimensional image data set for at least one loading state; and
an evaluation unit configured to reconstruct a three-dimensional combination image data set free of movement artefacts using a model-based reconstruction algorithm reproducing a movement taking place on the joint between the different loading states determine, by an evaluation of the three-dimensional combination image data set, the at least one joint load information item, wherein the at least one joint load information item comprises a four-dimensional movement data set of the joint,
wherein a loading is used as a fourth dimension in addition to three spatial dimensions,
wherein the loading varies according to a movement of the patient, and
wherein a change in the four-dimensional movement data set of the joint corresponds to a change in the loading.

21. The imaging apparatus of claim 20, wherein the imaging apparatus is an X-ray apparatus.

22. The imaging apparatus of claim 20, further comprising:
a patient couch configured to set the different loading states of the joint of the patient, the patient couch comprising a supporting surface for the patient tiltable about a rotation axis in such a way that the patient is movable, by the tilting of the patient couch, between a lying state in which the joint is under minimal loading and a standing state in which the joint is under maximal loading, wherein the patient couch has a rotation axis arranged close to a floor at a foot-side end of the supporting surface.

23. A non-transitory computer readable medium storing thereon a computer program code, which, when executed by a processor of a computing device, causes the computing device to at least perform:
record a plurality of image data sets of a joint of a patient for different loading states by an imaging apparatus wherein the plurality of image data sets comprises at least one three-dimensional image data set for at least one loading state;
reconstruct, using a model-based reconstruction algorithm reproducing a movement taking place on the joint between the different loading states, a three-dimensional combination image data set free of movement artefacts; and
determine, by an evaluation of the three-dimensional combination image data set, the at least one joint load information item, wherein the at least one joint load information item comprises a four-dimensional movement data set of the joint,
wherein a loading is used as a fourth dimension in addition to three spatial dimensions,
wherein the loading varies according to a movement of the patient, and wherein a change in the four-dimensional movement data set of the joint corresponds to a change in the loading.

* * * * *